United States Patent [19]
Martin

[11] Patent Number: 5,584,812
[45] Date of Patent: Dec. 17, 1996

[54] CLOSED INTRAVENOUS SYSTEM

[75] Inventor: Linda R. Martin, Macomb Township, Mich.

[73] Assignee: Stonefield Medical Products, Inc., Pittsford, N.Y.

[21] Appl. No.: 358,237

[22] Filed: Dec. 16, 1994

[51] Int. Cl.$^6$ .................................................. A61M 5/00
[52] U.S. Cl. ........................................... 604/164; 604/280
[58] Field of Search ..................................... 604/158, 161, 604/164, 165, 167, 280

[56] References Cited

U.S. PATENT DOCUMENTS

| | | | |
|---|---|---|---|
| 3,565,074 | 2/1971 | Foti | 604/164 |
| 4,417,886 | 11/1983 | Frankhouser et al. | 604/164 X |
| 4,772,266 | 9/1988 | Groshong | 604/164 |
| 5,368,574 | 11/1994 | Antonacci et al. | 604/164 |
| 5,380,292 | 1/1995 | Wilson | 604/164 |

OTHER PUBLICATIONS

Prior Art IV Product of Critikon, Tampa, FL 33634, Date Unknown But Believed At Least As Early As Dec. 15, 1993.
Prior Art Baxter Fitting Product Of Health Care Corp. Deerfield, IL 60015 Date Unknown But Believed at Least As Early As Dec. 15, 1993.
Prior Art Coupling Product Of Becton–Dickenson Co., Franklin Lakes, NJ 07417, Date Unknown, But Believed At Least As Early As Dec. 15, 1993.
Prior Art IV "T" Fitting Product Of Mendex, Inc. Hilliard, OH 43026 Date Unknown But Believed At Least As Early As Dec. 15, 1993.
"Preventing Needlesticks" By Inge Gurevich, *RN*, pp. 44–49, Nov. 1994.

*Primary Examiner*—Sam Rimell
*Attorney, Agent, or Firm*—Cumpston & Shaw

[57] ABSTRACT

A closed intravenous (IV) system includes a needle member and a sleeve member, wherein the sleeve member is provided with a resilient seal so that blood is contained after withdrawal of the needle member from the sleeve member. In a first preferred form of the closed IV system, the needle of the needle member extends through a resilient stopper of a fitting and the tip portion of the needle protrudes outwardly from the sleeve. The needle member is withdrawn after a patient's vein has been pierced. In a second preferred form of the closed IV system, the sleeve member is provided with a seal and the needle member is received by the sleeve member, wherein a tip portion of the needle protrudes outwardly from the sleeve. The needle member is withdrawn after a patient's vein has been pierced. A fitting is then snapped into place onto the sleeve member after a downstream IV apparatus has been pre-connected thereto.

10 Claims, 3 Drawing Sheets

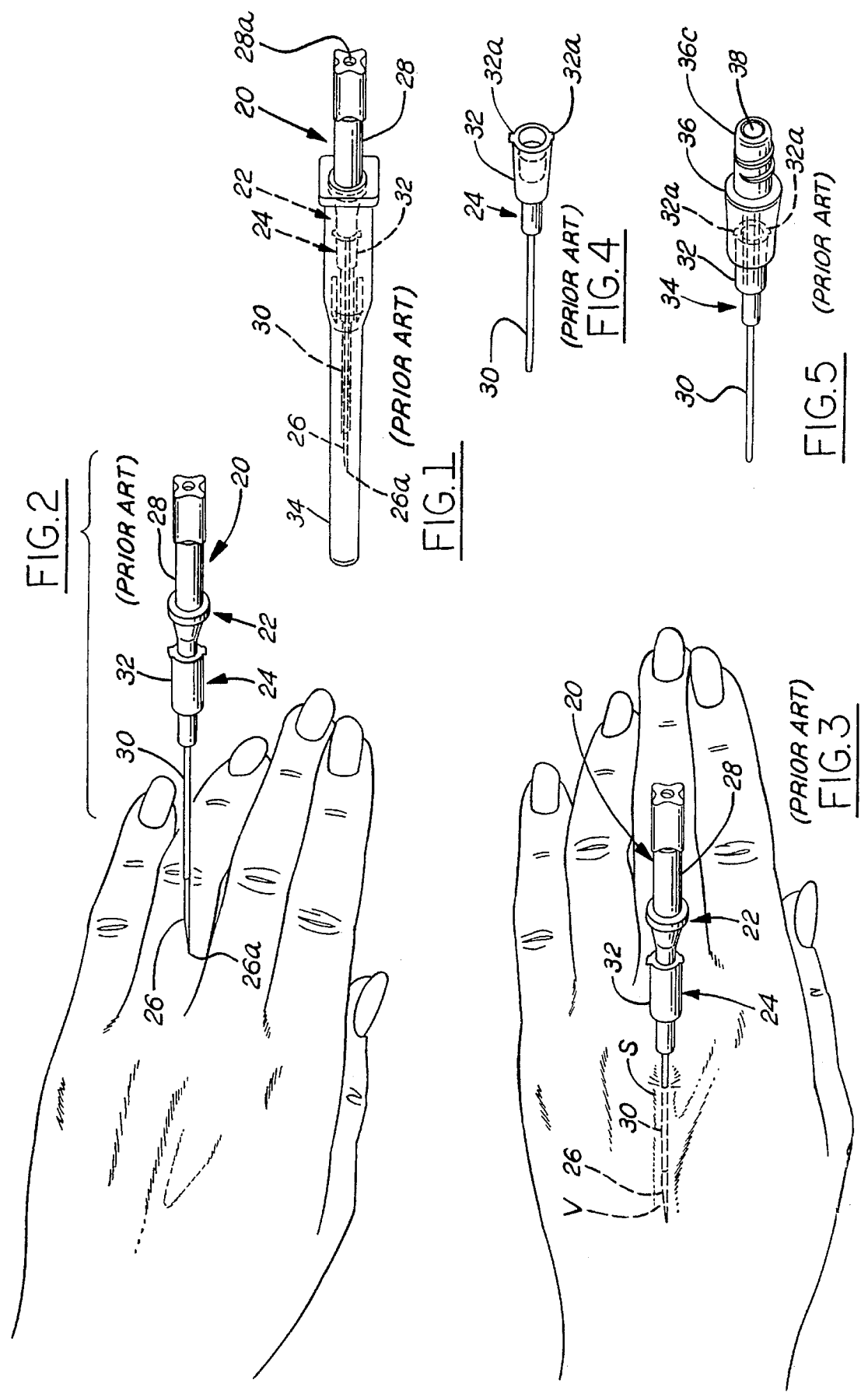

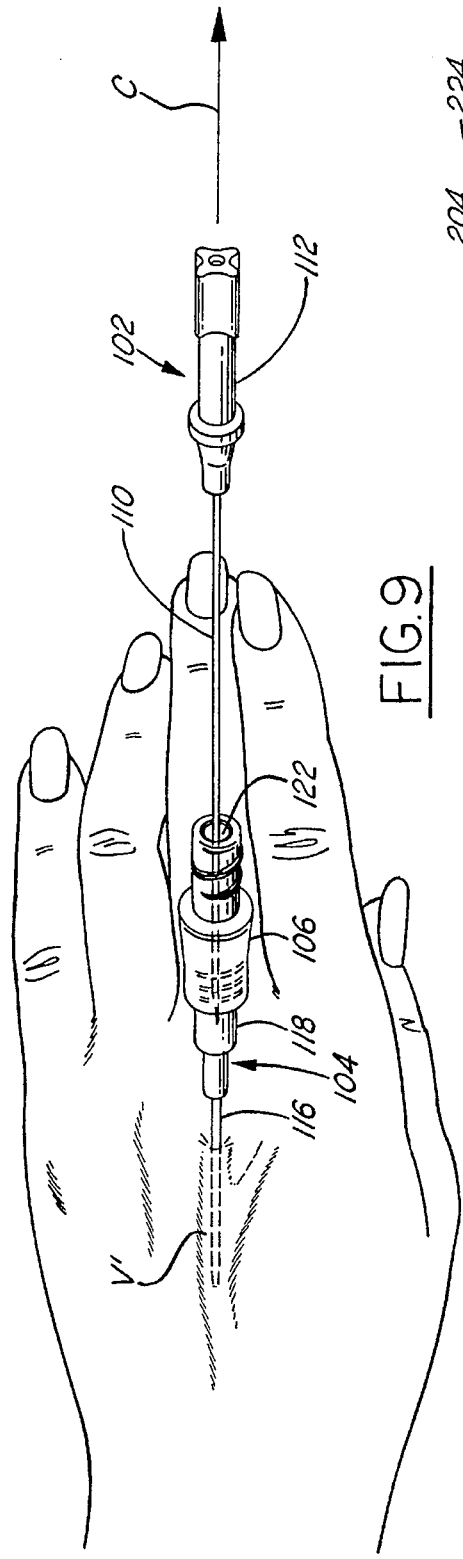
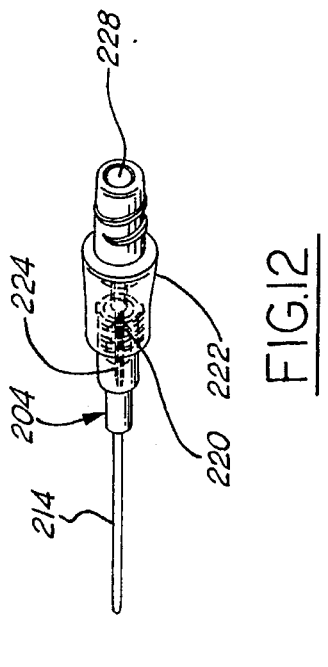
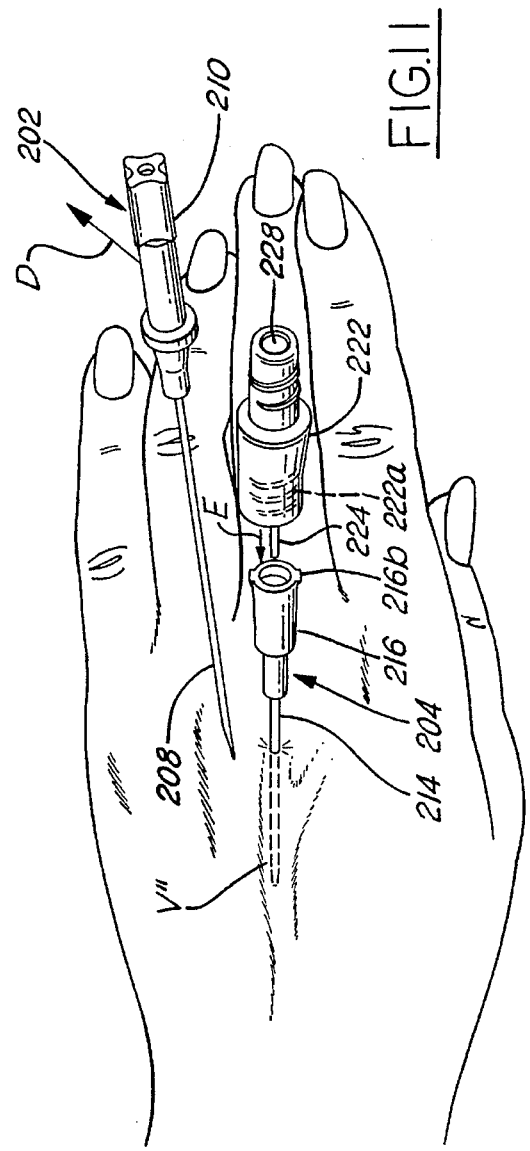

CLOSED INTRAVENOUS SYSTEM

BACKGROUND OF THE INVENTION

1. Field of the Invention

The present invention relates to intravenous systems used in the medical arts, and more particularly to an intravenous system which is at all times closed so that the patient's blood is at all times contained within the intravenous system.

2. Description of the Prior Art

Medical patients are frequently in need of intravenous (IV) procedures wherein a needle is utilized to pierce the patient's skin and a selected vein to thereby gain access to the patient's circulatory system. IV procedures are an extremely common and important aspect of medical practice for a multitude of compelling reasons, such as for example to extract blood for sampling and testing purposes, or for introducing one or more fluids into the patient's circulatory system.

FIGS. 1 through 7 depict the conventional IV system in terms of both the conventional IV apparatus and the conventional procedure of use of the conventional IV apparatus.

As shown in FIG. 1, the conventional IV apparatus 20 is composed of a needle member 22 and a sleeve member 24. The needle member 22 is composed of a medical needle 26 sealingly anchored to a plastic needle head 28. The needle 26 and the needle head 28 each have a mutually communicating first passageway P1 so that blood may flow through the needle into and through the needle head, wherein the needle head is porousably plugged at its terminous remote from the needle by a plug 28a. The sleeve member 24 is composed of a flexible plastic sleeve 30 sealingly anchored to a plastic sleeve head 32. The sleeve 30 and the sleeve head 32 each have a mutually communicating second passageway P2 so that blood may flow through the sleeve into and through the sleeve head. The sleeve 30 is dimensioned to coaxially receive therein the needle 26 and the sleeve head 32 is structured to receive the needle head 28 adjacent the needle. A plastic protective capsule 34 snappingly engages with the needle head 28 so as to protectively receive therein the needle 26, the sleeve 30 the sleeve head 32 and a portion of the needle head 28 adjacent the needle.

The conventional procedure for use of the conventional IV apparatus 20 is depicted in FIGS. 2 through 7.

A caregiver first ascertains a suitable vein V of the patient, and then uses the conventional IV apparatus 20 to fluidically access the vein. As depicted in FIG. 2, this procedure involves grasping the sleeve head 32 and needle head 28 and thereupon causing the needle 26 and its surrounding sleeve 30 to pierce the skin S and the vein V sufficiently that the sleeve is well inside the vein, as shown in FIG. 3. In this regard, the needle 26 provides the necessary rigidity and sharpness to effect the penetration; accordingly for this reason, the sleeve 30 is offset from the needle tip 26a.

Because the needle 26 is too rigid to be left in the patient for an extended time (accidental movements of the needle have the potential of causing trauma to the vein area), it is next necessary to extract the needle 26 so that only the sleeve 30 is left in the vein V. In this regard, the caregiver then extracts the needle member 22 slidingly in relation to the sleeve member 24 until it is free therefrom, as shown in FIG. 6 (the separational movement being represented by arrow A).

Once the needle 26 is extracted, blood from the vein V will spurt freely through the second passageway P2 and externally out the sleeve head 32. Quickly, therefore, the caregiver must install a fitting 36 onto the sleeve head 32 (in the direction of arrow B in FIG. 6) in order to stop blood spillage. In this regard, as shown in FIGS. 4 and 5, the sleeve head is provided with wings 32a which threadably engage internal threads 36a of the fitting 36. As shown best by FIG. 7, the fitting 36 is provided with a centrally disposed tubular projection 36b which sealingly abuts a gently conically shaped inside wall 32b of the sleeve head 32. While the fitting 36 has a third passageway P3 therein which fluidically communicates with the second passageway P2 of the sleeve member 24, blood is prevented from escaping therefrom by action of a resistent stopper 38 located at the remote end 36c of the fitting. Now a coupling 40 having a proboscis 42 and a clip 44, wherein the clip engages the fitting 36 when the proboscis has pierced the resistent stopper 38 and fluidically communicates with the vein via the second and third passageways P2, P3. A receptacle 46 on the coupling 40 sealingly receives an external IV line L.

While the above recounted conventional IV system provides a medically sound modality for providing an IV, it has associated with it a potential danger and mess occasioned because the conventional IV system is open between the time the needle member is extracted from the sleeve member and the fitting is connected with the sleeve head. Accordingly, what is needed is an IV system which is at all times closed.

SUMMARY OF THE INVENTION

The present invention is an intravenous (IV) system which is at all times closed so that blood of a patient is at all times contained. The IV system according to the present invention includes a needle member and a sleeve member, wherein the sleeve member is provided with a resilient seal so that blood is contained after withdrawal of the needle member from the sleeve member.

In a first preferred form of the IV system according to the present invention, the needle member is similar to a conventional needle member, wherein a medical needle is sealingly anchored to a needle head and a first passageway is located therein, except that the needle is additionally elongated. Further, the sleeve member is similar to that of a conventional sleeve member, wherein a flexible sleeve is sealingly anchored to a sleeve head and a second passageway is located therein. Still further, a fitting similar to a conventional fitting is pre-attached to the sleeve head. In operation, the needle of the needle member extends through the resilient stopper of the fitting and the tip portion of the needle protrudes outwardly from the sleeve. The needle member is withdrawn after a patient's vein has been pierced.

In a second preferred form of the IV system according to the present invention, the needle member is similar to a conventional needle member. Further, a modified sleeve member includes a resistent sleeve stopper situated in the sleeve head. Still further, a modified fitting includes a fitting proboscis which pierces sealingly through the sleeve stopper in order to gain access to the patient's circulatory system. In operation, the needle member is received by the sleeve member, wherein a tip portion of the needle protrudes outwardly from the sleeve. The needle member is withdrawn after a patient's vein has been pierced. The fitting is then snapped into place onto the sleeve head after the downstream IV apparatus has been pre-connected thereto.

Accordingly, it is an object of the present invention to provide a completely closed intravenous (IV) system, wherein blood of the patient is at all times contained.

It is a further object of the present invention to provide a method of using IV apparatus to thereby provide a closed system in which patient blood cannot exit to the environs thereabout.

It is an additional object of the present invention to utilize a resistent stopper situated in a sleeve head of a sleeve member to thereby prevent patient blood from exiting the sleeve head other than via an intended route within the IV system.

These, and additional objects, advantages, features and benefits of the present invention will become apparent from the following specification.

BRIEF DESCRIPTION OF THE DRAWINGS

In the Figures, FIGS. 1 through 7 depict prior art IV apparatus and the methodology of use thereof; the remaining Figures depict the IV system according to the present invention, wherein:

FIG. 1 is a perspective view of a conventional IV apparatus located in its capsule;

FIG. 2 is a perspective view of the conventional IV apparatus about to be used;

FIG. 3 is a perspective view of the conventional IV apparatus in use piercing a patient's vein;

FIG. 4 is a perspective view of a conventional sleeve member;

FIG. 5 is a perspective view of a conventional sleeve member mated to a conventional fitting;

FIG. 6 is a perspective view of the conventional IV apparatus, depicting steps of use thereof wherein a needle member is withdrawn from a sleeve member and a fitting is mated to the sleeve member;

FIG. 7 is a sectional side view of the conventional IV apparatus shown in operation with respect to a patient's vein and seen along line 7—7 in FIG. 6, wherein connected thereto is a conventional fitting, in turn, connected thereto is a conventional coupling;

FIG. 9 is a perspective view of the first form of the IV system according to the present invention, shown in operation;

FIG. 11 is a perspective view of the second form of the IV system according to the present invention, shown in operation; and FIG. 12 is a perspective view of a mated sleeve member and fitting according to the second form of the IV system according to the present invention.

DETAILED DESCRIPTION OF THE PREFERRED EMBODIMENT

Figure 8:
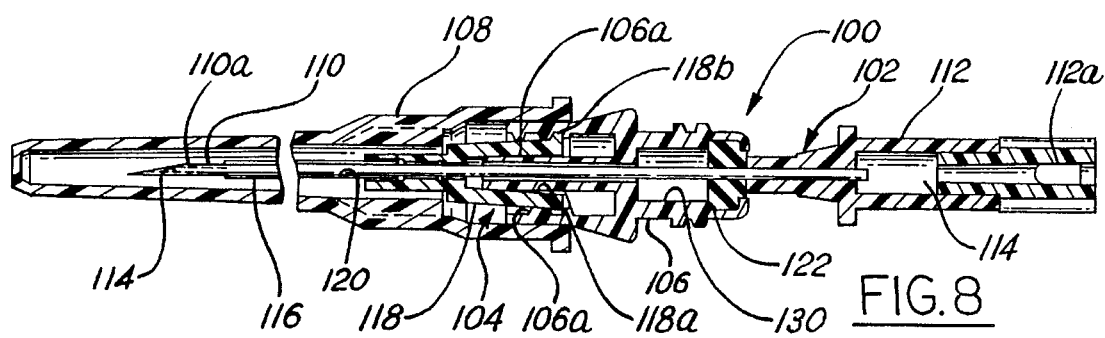
FIG. 8 is a sectional side view of a first form of the IV system according to the present invention.

Referring now to FIGS. 8 and 9, the first preferred form of the IV system 100 according to the present invention will be detailed. The IV system 100 includes a needle member 102, a sleeve member 104 and a fitting 106. These components are preassembled as shown in FIG. 8, wherein the needle member 102 is snappingly engaged with respect to an encapsulation member 108.

The needle member 102 is structured similarly to a conventional needle member as recounted hereinabove, wherein a metallic medical needle 110 is sealingly anchored to a plastic needle head 112 and a first passageway 114 is located within and along the needle member, except that the needle is provided with an additional elongation for cooperating with a sleeve member, as will become clear momentarily. The needle head 112 includes a porous plug 112a situated at its remote end.

The sleeve member 104 is structured similarly to that of a conventional sleeve member as recounted hereinabove, wherein a flexible plastic sleeve 116 is sealingly anchored to a plastic sleeve head 118 and a second passageway 120 is located within and along the sleeve member.

The fitting 106 is structured similarly to that of a conventional fitting as recounted hereinabove, inclusive of a resistent stopper 122, and is pre-attached threadably to the sleeve head in a conventional manner via mutual engagement of threads 106a and wings 118b, wherein the centrally disposed tubular projection 106a of the fitting seals against the inside wall 118a of the sleeve head 118. The fitting 106 has a thud passageway 130 therein. As detected in FIG. 8, when the needle head 112 is adjacent the resistent stopper 122 of the fitting 106, the needle 110 is sufficiently elongated so that it extends coaxially all along the sleeve 116 and a tip portion 110a thereof projects outwardly from the sleeve.

In operation, the needle 110 of the needle member 102 extends through the resistent stopper 122 of the fitting 106 and coaxially through the sleeve 116 and sleeve head 118, wherein the tip portion 110a of the needle protrudes outwardly from the sleeve. After removal from the encapsulation member 108, the needle member and the fitting are carefully held, a vein selected, and the needle and its associated sleeve are then caused to pierce the patient's skin and the selected vein V'. Once the sleeve is lodged in the vein (or other body part such as an artery), the needle member is withdrawn along arrow C from the sleeve member and the fitting, as shown in FIG. 9. Because the fitting is pre-attached to the sleeve member, none of the patient's blood has exited to the external environs during the installation of the IV. Now a coupling may be installed onto the fitting in a conventional manner, again with no blood leakage occurring.

Figure 10:
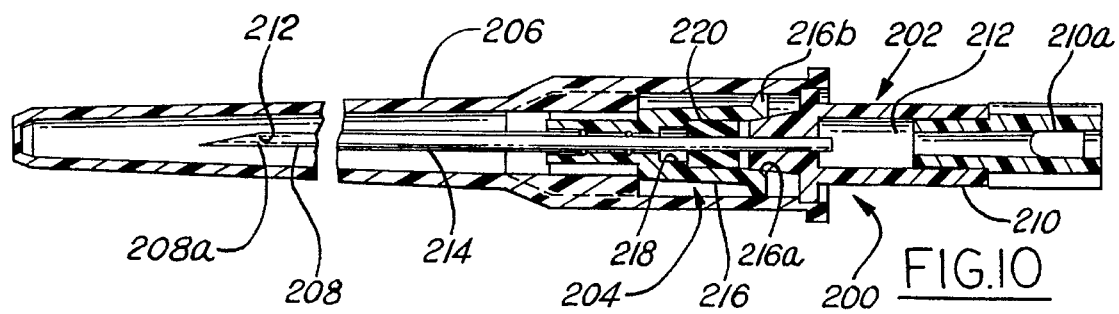
FIG. 10 is a sectional side view of a second form of the IV apparatus according to the present invention.

Referring now to FIGS. 10 through 12, the second preferred form of the IV system 200 according to the present invention will be detailed. The IV system 200 includes a needle member 202 and a sleeve member 204. These components are preassembled as shown In FIG. 10, wherein the needle member 202 is snappingly engaged with respect to an encapsulation member 206.

The needle member 202 is structured similarly to a conventional needle member as recounted hereinabove, wherein a metallic medical needle 208 is sealingly anchored to a plastic needle head 210 and a first passageway 212 is located within and along the needle member. The needle head 210 includes a porous plug 210a situated at its remote end.

The sleeve member 204 is structured similarly to that of a conventional sleeve member as recounted hereinabove, wherein a flexible plastic sleeve 214 is sealingly anchored to a plastic sleeve head 216 and a second passageway 218 is located within and along the sleeve member, except the sleeve head now includes a resistent sleeve stopper 220. The sleeve head 216 is dimensioned to receive a portion of the needle head 210 adjacent the needle 208. As depicted in FIG. 10, when the needle head 210 is received by the sleeve head 216, the needle 208 is sufficiently elongated so that it extends coaxially all along the sleeve 214 and a tip portion 208a thereof projects outwardly from the sleeve.

In operation, the needle 208 of the needle member 202 extends through the resilient sleeve stopper 220 of the sleeve head 216 and coaxilly through the sleeve 216 head and sleeve 214, wherein the tip portion 208a of the needle protrudes outwardly from the sleeve. After removal from the encapsulation member 206, the needle member and the sleeve member are carefully held, a vein selected, and the needle and its associated sleeve are then caused to pierce the patient's skin and the selected vein V" (or other body part such as an artery). Once the sleeve is lodged in the vein, the needle member is withdrawn from the sleeve member, as shown in FIG. 11 (the removal being represented by arrow D). Because the sleeve head is provided with a resilient stopper, none of the patient's blood has exited to the external environs after removal of the needle member.

Now in order to secure operation of the IV, a fitting 222 is provided which is structured similarly to that of a conventional fitting as recounted hereinabove, except that the centrally disposed tubular projection described hereinabove is now replaced by a fitting proboscis 224 which pierces sealingly through the resilient sleeve stopper 220 (when moved in the direction of arrow E in FIG. 11) in order to gain access to the patient's circulatory system. The fitting 222 and the sleeve member 204 are mutually threadably engaged in a conventional manner via mutual engagement of threads 222a and wings 216b. The fitting 222 has a third passageway therein. The fitting 222 further has a resilient fitting stopper 228. Now a coupling may be installed onto the fitting 222 in a conventional manner via sealing engagement with the resilient stopper 228, again with no blood leakage occurring provided the downstream IV apparatus has been pre-connected thereto.

Figure 6:
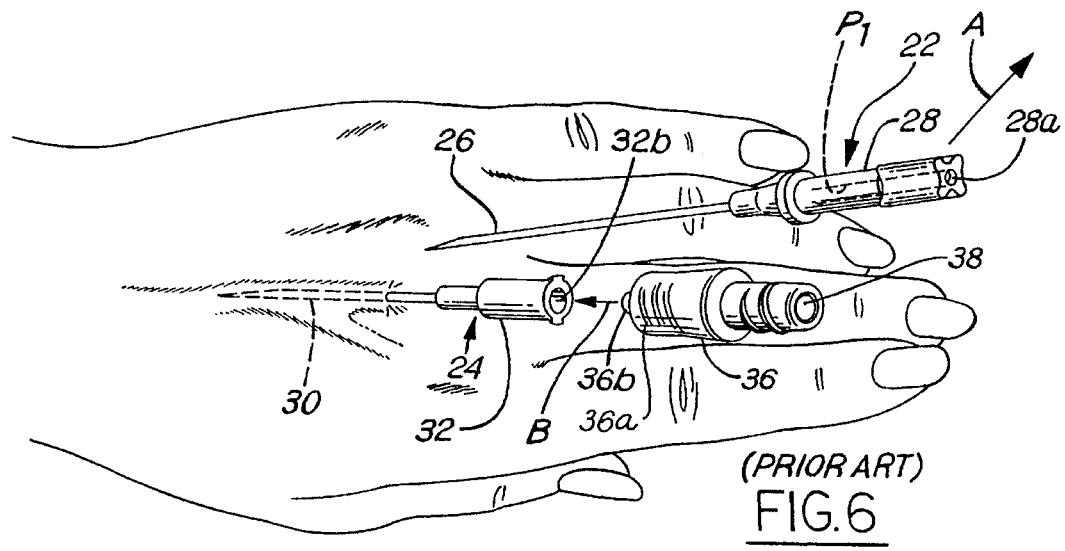
Figure 7:
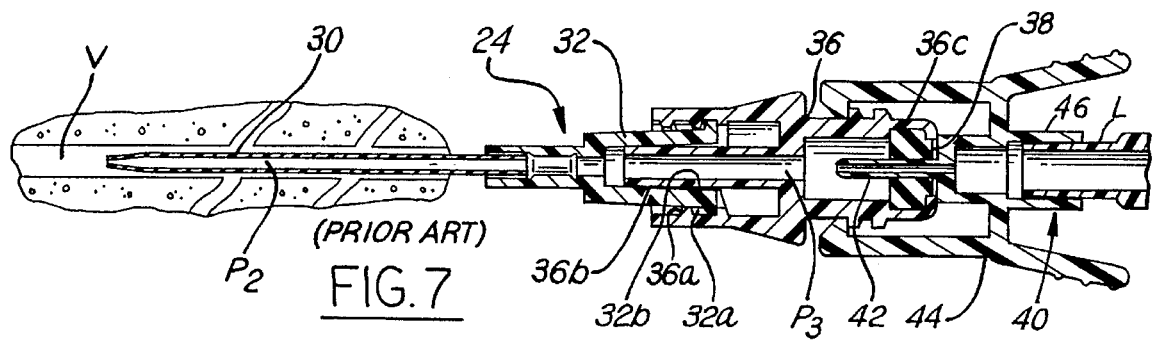

It will be appreciated that the fitting 222 may or may not have a resilient fitting stopper 228, in that the resilient sleeve stopper 220 renders the resilient fitting stopper redundant. Accordingly, the fitting may be open ended and connect directly with an external IV line in the manner indicated of the coupling 40 in FIG. 7; that is, the fitting is modified to include a receptacle (like receptacle 46) that sealingly receives an external IV line (like IV line L).

To those skilled in the art to which this invention appertains, the above described preferred embodiment may be subject to change or modification. For example, the fittings depicted in the Drawing are by way only of preferred example; it is known in the art to provide fittings in the form of a "T", and such structural aspects are considered within ordinary skill to substitute for the exact fitting structures depicted herein. Further for example, the sleeve head can be permanently sealingly connected with, or integrally connected with, the fitting in the first preferred form of the present invention. Such change or modification can be carried out without departing from the scope of the invention, which is intended to be limited only by the scope of the appended claims.

What is claimed is:

1. A closed intravenous system comprising:

a needle member comprising:

a first needle having a tip; and a needle head sealingly connected with said first needle opposite said tip, and a first passageway extending through said first needle and said needle head;

a sleeve member comprising:

a sleeve dimensioned to coaxially receive therein said first needle; and a sleeve head sealingly connected with said sleeve, and a second passageway extending through said sleeve and said sleeve head;

a fitting having a tubular projection at one end and a resilient stopper at an opposite end of the fitting, and a third passageway extending through said fitting, said third passageway being selectively sealed by said resilient stopper; and a connector for sealingly connecting said tubular projection of said fitting to said sleeve head so that said second and third passageways mutually fluidically communicate;

wherein when said fitting is sealingly connected with said sleeve head and said needle head is located adjacent said resilient stopper of said fitting, said first needle extends coaxially through said sleeve, and a portion of said first needle adjacent said tip projects outwardly from said sleeve.

2. The closed intravenous system of claim 1, further comprising external intravenous apparatus and a coupling having a second needle removably sealingly piercing said resilient stopper to thereby fluidically communicate with said third passageway.

3. A closed intravenous system comprising:

a needle member comprising:

a needle having a tip; and a needle head sealingly connected with said needle opposite said tip, and a first passageway extending through said needle and said needle head;

a sleeve member comprising:

a sleeve dimensioned to coaxially receive said needle; and a sleeve head sealingly connected with said sleeve, and a second passageway extending through said sleeve and said sleeve head, said sleeve head having a resilient sleeve stopper for selectively sealing said second passageway with respect to said first passageway;

a fitting having a proboscis at one end thereof, and a third passageway extending through said fitting; and means for connecting said proboscis of said fitting to said sleeve head so that said proboscis sealingly pierces said resilient sleeve stopper to thereby provide fluidic communication between said second and third passageways;

wherein when said fitting is not connected with said sleeve head, and said needle head is located adjacent said sleeve head, said needle extends coaxially through said sleeve and a portion of said needle adjacent said tip projects outwardly from said sleeve.

4. The closed intravenous system of claim 3, wherein said fitting has resilient fitting stopper means for selectively sealing said third passageway.

5. The closed intravenous system of claim 3, wherein said fitting provides coupling means for sealingly connecting an external intravenous apparatus to said fitting.

6. A method for performing a closed intravenous procedure on a vein of a patient to provide fluidic communication with the venous blood of the patient, comprising the steps of:

providing a sleeve having a first passageway extending therethrough;

providing a fitting having one end and an opposite end connected by a second passageway, the second passageway communicating with the first passageway at the one end;

resiliently sealing said second passageway with a resilient stopper at the opposite end;

providing a first needle having a tip;

piercing said seal with the first needle and passing the first needle coaxially through said fitting and said sleeve whereupon a portion of said first needle adjacent said tip projects from said sleeve;

piercing a selected vein of a patient with the needle tip and sleeve; and withdrawing said first needle from said sleeve to thereby provide an intravenous engagement of said sleeve with respect to said vein.

7. The method of claim 6, further comprising the step of sealingly connecting an external intravenous apparatus to said sleeve.

8. A method for performing a closed intravenous procedure on a vein of a patient to provide fluidic communication with the venous blood of the patient, comprising the steps of:

providing a sleeve having a passageway extending therethrough;

resiliently sealing said passageway;

providing a first needle having a tip:

piercing said seal with the first needle and passing the first needle coaxially through said sleeve whereupon a portion of said first needle adjacent said tip projects from said sleeve;

piercing a selected vein of a patient with the needle tip and sleeve;

withdrawing said first needle from said sleeve to thereby provide an intravenous engagement of said sleeve with respect to said vein, wherein said seal prevents blood the patient from exiting said sleeve;

providing a second needle shorter than the first needle;

coupling the second needle to an external intravenous apparatus; and piercing the seal with the second needle to form a fluid path between the external intravenous apparatus and the vein.

9. A closed intravenous system comprising:

a needle member comprising;

a first needle having a tip; and a needle head sealingly connected with said first needle opposite said tip, and a first passageway extending through said first needle and said needle head;

a sleeve member comprising:

a sleeve dimensioned to coaxially receiving therein said first needle; and a sleeve head sealingly connected with said sleeve, and a second passageway extending through said sleeve and said sleeve head;

a fitting having a tubular projection at one end and a resilient stopper at an opposite end of the fitting, and a third passageway extending through said fitting, said third passageway being selectively sealed by said resilient stopper;

a connector for sealingly connecting said tubular projection of said fitting to said sleeve head so that said second and third passageways mutually fluidically communicate;

a second needle shorter than the first needle; and external intravenous apparatus connected to the second needle;

wherein when said fitting is sealingly connected with said sleeve head and said needle head is located adjacent said resilient stopper of said fitting, said first needle extends coaxially through said sleeve, and a portion of said first needle adjacent said tip projects outwardly from said sleeve; and wherein the external intravenous apparatus can be coupled to the sleeve member by passing the second needle through the resilient stopper.

10. A closed intravenous system comprising;

a first needle member comprising;

a needle having a tip; and a needle head sealingly connected with said first needle opposite said tip thereof, and a first passageway extending through said first needle and said needle head;

a sleeve member comprising;

a sleeve dimensioned to coaxially receive said first needle; and a sleeve head sealingly connected with said sleeve, and a second passageway extending through said sleeve and said sleeve head, said sleeve head having a resilient sleeve stopper for selectively sealing said second passageway with respect to said first passageway;

second needle shorter than the first needle; and external intravenous apparatus connected to the second needle;

wherein when said needle head is located adjacent said sleeve head, said first needle extends coaxially through said sleeve and a portion of said first needle adjacent said tip projects outwardly from said sleeve; and wherein the external intravenous apparatus can be coupled to the sleeve member by passing the second needle through the resilient sleeve stopper.

* * * * *

UNITED STATES PATENT AND TRADEMARK OFFICE
CERTIFICATE OF CORRECTION

PATENT NO. : 5,584,812  Page 1 of 2
DATED : December 17, 1996
INVENTOR(S) : MARTIN It is certified that error appears in the above-indentified patent and that said Letters Patent is hereby corrected as shown below:

Column 2, lines 12, 15 and 55, and
Column 3, line 6, and
Column 4, lines 14, 20, 25 and 61

"resistent", each occurrence, should read -- resilient --

Column 4, line 19

"thud" should read -- third --.

Column 4, line 19

"detected" should read -- depicted --.

Claim 8, line 29

"the patient" should read -- of the patient --.

Claim 10, line 23

"a first needle member" should read -- a needle member --

Claim 10, line 24

"a needle" should read -- a first needle --.

UNITED STATES PATENT AND TRADEMARK OFFICE
CERTIFICATE OF CORRECTION

PATENT NO. : 5,584,812
DATED : December 17, 1996
INVENTOR(S) : MARTIN

It is certified that error appears in the above-indentified patent and that said Letters Patent is hereby corrected as shown below:

Claim 10, line 36

"second needle" should read -- a second needle --.

Signed and Sealed this

Twenty-second Day of April, 1997

Attest:

BRUCE LEHMAN

*Commissioner of Patents and Trademarks*

*Attesting Officer*